(12) United States Patent
Gordon et al.

(10) Patent No.: US 7,297,137 B2
(45) Date of Patent: Nov. 20, 2007

(54) METHOD OF DETECTING SURGICAL EVENTS

(75) Inventors: Raphael Gordon, San Dimas, CA (US); Michael D. Morgan, Costa Mesa, CA (US)

(73) Assignee: Alcon, Inc., Hunenberg (CH)

(*) Notice: Subject to any disclaimer, the term of this patent is extended or adjusted under 35 U.S.C. 154(b) by 841 days.

(21) Appl. No.: 10/818,314

(22) Filed: Apr. 5, 2004

(65) Prior Publication Data

US 2005/0209561 A1   Sep. 22, 2005

Related U.S. Application Data

(60) Provisional application No. 60/555,240, filed on Mar. 22, 2004.

(51) Int. Cl.
*A61M 1/00* (2006.01)

(52) U.S. Cl. .................................................. 604/119

(58) Field of Classification Search ............ 604/119, 604/118, 268, 313, 315, 316, 524, 264, 65, 604/66, 67; 128/DIG. 12, 13
See application file for complete search history.

(56) References Cited

U.S. PATENT DOCUMENTS

| | | | |
|---|---|---|---|
| 3,589,363 | A | 6/1971 | Banko et al. |
| 4,223,676 | A | 9/1980 | Wuchinich |
| 4,246,902 | A | 1/1981 | Martinez |
| 4,493,694 | A | 1/1985 | Wuchinich |
| 4,515,583 | A | 5/1985 | Sorich |
| 4,589,415 | A | 5/1986 | Haaga |
| 4,609,368 | A | 9/1986 | Dotson, Jr. |
| 4,827,911 | A | 5/1989 | Broadwin et al. |
| 4,869,715 | A | 9/1989 | Sherburne |
| 4,922,902 | A | 5/1990 | Wuchinich et al. |
| 4,989,583 | A | 2/1991 | Hood |
| 5,154,694 | A | 10/1992 | Kelman |
| 5,359,996 | A | 11/1994 | Hood |
| 5,591,127 | A | 1/1997 | Barwick, Jr. et al. |
| 5,700,240 | A | 12/1997 | Barwick, Jr. et al. |
| 5,766,146 | A | 6/1998 | Barwick, Jr. |
| 6,027,515 | A | 2/2000 | Cimino |
| 6,179,808 | B1 | 1/2001 | Boukhny et al. |

*Primary Examiner*—Manuel Mendez
(74) *Attorney, Agent, or Firm*—Jeffrey S. Schira

(57) ABSTRACT

A surgical system that is able to sense the onset of an occlusion or other surgical event as well as the instant an occlusion breaks.

20 Claims, 1 Drawing Sheet

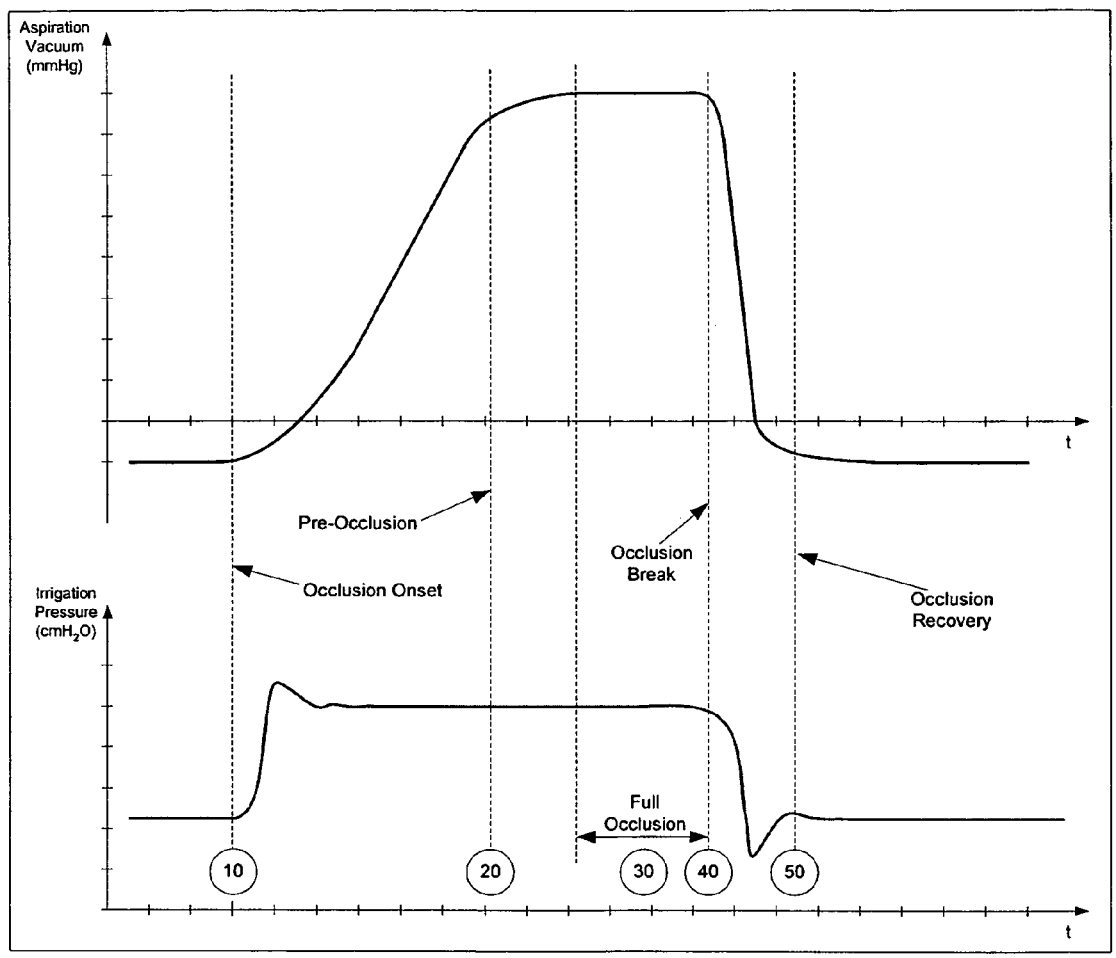

METHOD OF DETECTING SURGICAL EVENTS

This application claims the benefit of U.S. Provisional Application Ser. No. 60/555,240, filed Mar. 22, 2004.

BACKGROUND OF THE INVENTION

This invention relates generally to the field of cataract surgery and more particularly to a surgical parameters control method for use with a phacoemulsification system.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

The preferred surgical technique is to make the incision into the anterior chamber of the eye as small as possible in order to reduce the risk of induced astigmatism. These small incisions result in very tight wounds that squeeze the irrigating sleeve tightly against the vibrating tip. Friction between the irrigating sleeve and the vibrating tip generates heat, but the risk of the tip overheating and causing a burn to the tissue is reduces by the cooling effect of the aspirated fluid flowing inside the tip. When the tip becomes occluded with tissue, this aspiration flow can be reduced or eliminated, allowing the tip to heat up. In addition, during occlusion, a larger vacuum can build up in the aspiration tubing so that when the occlusion breaks, a larger amount of fluid can be quickly suctioned from the eye, possibly resulting a in the globe collapsing.

Prior art devices have used sensors that detect large rises in aspiration vacuum, and detect occlusions based on vacuum rise. Based on this sensed occlusion, power to the handpiece may be reduced and/or irrigation and aspiration flows can be increased. See U.S. Pat. Nos. 5,591,127, 5,700,240 and 5,766,146 (Barwick, Jr., et al.) and U.S. Pat. No. 6,179,808 B1 (Boukhny, et al.), the entire contents of which being incorporated herein by reference. These devices, however, used a fixed aspiration vacuum level to trigger a response from the system. This fixed level is a threshold value based upon a fixed percentage of the selected upper vacuum limit. In such systems, the system does not respond until that preset vacuum level is reached. In reality, the vacuum level increase and, during occlusion break, decrease, occur over a short period of time. Setting this preset vacuum limit too low results in the system changing its operating parameters prematurely, and holding on to those parameters after the occlusion has cleared. Setting the limit too high can result in the system changing its setting too close to the actual occurrence of the occlusion, and changing its setting back to normal prior to the clearance of the occlusion.

Therefore, a need continues to exist for an occlusion detection method that more accurately detects the occurrence and clearance of an occlusion in a surgical aspiration system.

BRIEF SUMMARY OF THE INVENTION

The present invention improves upon the prior art by providing a surgical system that is able to sense the onset of an occlusion or other surgical event as well as the instant an occlusion breaks. The inventors have determined that the rate of change in the pressure level in an aspiration or irrigation system can be used to detect an occlusion occurrence. By monitoring the rate of change in the aspiration or irrigation pressure level, occlusion onset and break up can be accurately detected.

Accordingly, one objective of the present invention is to provide a surgical console control system.

Another objective of the present invention is to provide a surgical console control system having a method for detecting an occlusion in an aspiration line.

Another objective of the present invention is to provide a method for detecting an occlusion.

Another objective of the present invention is to provide a for detecting an occlusion event.

These and other advantages and objectives of the present invention will become apparent from the detailed description and claims that follow.

BRIEF DESCRIPTION OF THE DRAWINGS

The figure is a representation of a typical aspiration and irrigation pressure plots made during an occlusion event.

DETAILED DESCRIPTION OF THE INVENTION

The inventors have discovered that the aspiration and irrigation pressure levels during an occlusion event follows a detectable pattern. Occlusion onset event 10 is characterized by a rapid increase in aspiration vacuum and irrigation pressure (respective rates are >0). Preocclusion event 20 is characterized by a slowing of the positive increase in vacuum and irrigation pressure (a gradual rate decrease to approximately 0). Occlusion period 30 is characterized by a constant vacuum rate (vacuum rate=0). Occlusion break event 40 is characterized by a rapid decrease of aspiration vacuum and irrigation pressure (respective rates are <0). Occlusion recovery event 50 is characterized by a slowing of the decrease in vacuum and irrigation pressure (gradual rate increase to approximately 0). This pattern of aspiration vacuum and irrigation pressure increase and decrease during an occlusion event is consistent from surgical system to surgical system. The desired pattern recognition can be accomplished with a variety of known digital signal processing methods. One suitable method is correlation. By calculating a linear correlation between this predefined pattern and the actual aspiration or irrigation pressure sensor readings from the surgical system, all of these phases of an occlusion event can be detected.

For example, the linear correlation between two sequences $x_i$ and $y_i$ is a measurement of how close one sequence can be transformed into the other via a linear transformation:

$$y_i = ax_i + b$$

Where: a—linear correlation coefficient, b—offset.

Given two sequences, the linear correlation R is calculated as follows:

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}$$

Where: N—correlation length (i.e. number of points in the sequences).

The linear correlation coefficient is calculated as follows:

$$a = \frac{\sum_{i=0}^{N} x_i y_i - \frac{\sum_{i=0}^{N} x_i \sum_{i=0}^{N} y_i}{N}}{\sum_{i=0}^{N} x_i^2 - \frac{\left(\sum_{i=0}^{N} x_i\right)^2}{N}}$$

The method of the present invention includes calculating the linear correlation between a sample sequence of aspiration vacuum and/or irrigation pressure sensor readings collected during use of the surgical system and the predefined pattern representing the occlusion events in question. The calculated correlation value reflects the similarity between the sample sequence and the predefined pattern, with the highest possible value of 1.0 representing an absolute match. The preferred range of values indicating a sufficient for the application pattern match is typically between 0.80 and 0.99. Once the match is established, the certainty of the some surgical events such as pre-occlusion and occlusion recovery is high, and the surgical parameters of the system can be adjusted. For events such as occlusion onset and occlusion break the pattern match also needs to be qualified based on the rate of the change of the test values. The rate of change can be evaluated using linear correlation, which reflects the slope ratio of the test sequence and the predefined pattern, and can thus be used to evaluate whether the sample sequence has a sufficient rate of change for a particular event. Another method for evaluation the rate of change is a direct calculation of the derivative ($\Delta$Value/$\Delta$Time). The criteria for a sufficient rate can be established empirically for a given system at different settings (e.g. different aspiration pump rates). For the cases that require qualification on both pattern match and the rate of change, the occlusion event is considered to be detected when both conditions are satisfied. Once the occlusion event is detected the surgical parameters of the system can be adjusted. The described method can applied to detecting all events in occlusion make-to-break sequence (occlusion onset, pre-occlusion, occlusion, occlusion break, and recovery.)

One skilled in the art will recognize that the pattern match discussed above can be accomplished using convolution rather than correlation.

The method of the present invention can be implemented on commercially available surgical systems through appropriate hardware and software controls. One suitable system is the INFINTI® Vision System sold by Alcon Laboratories, Inc., Fort Worth, Tex. Other suitable systems are described in U.S. Pat. No. 6,179,808 B1 (Boukhny, et al.) and U.S. Pat. No. 6,261,283 (Morgan, et al.), the entire contents of which being incorporated herein by reference, such systems including a data storage device or memory.

This description is given for purposes of illustration and explanation. It will be apparent to those skilled in the relevant art that changes and modifications may be made to the invention described above without departing from its scope or spirit.

We claim:

1. A method of controlling a surgical system, the surgical system having a memory, comprising the steps of:
    a) storing at least one pre-determined pattern of aspiration vacuums in the surgical system memory;

b) operating the surgical system to perform a surgical procedure;
c) monitoring the aspiration vacuum in the surgical system during the surgical procedure;
d) calculating a linear correlation between the monitored aspiration vacuum and the pre-determined pattern of aspiration vacuums;
e) establishing a match between the monitored aspiration vacuum and the pre-determined pattern of aspiration vacuums based on the linear correlation;
f) detecting an occurrence of a surgical event based upon the establishment of the match between the monitored aspiration vacuum and the pre-determined pattern of aspiration vacuums; and
g) varying the operation of the surgical system based on the detection of the occurrence of the surgical event.

2. The method of claim 1 wherein the linear correlation between the monitored aspiration vacuum and the pre-determined pattern of aspiration vacuums is calculated using the following formula:

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}$$

where: N—correlation length (i.e. number of points in the sequences.

3. A method of controlling a surgical system, the surgical system having a memory, comprising the steps of:
a) storing at least one pre-determined pattern of aspiration vacuums and at least one a rate of change of aspiration vacuum in the surgical system memory;
b) operating the surgical system to perform a surgical procedure;
c) monitoring the aspiration vacuum in the surgical system during the surgical procedure;
d) calculating a linear correlation between the monitored aspiration vacuum and the pre-determined pattern of aspiration vacuums;
e) establishing a match between the monitored aspiration vacuum and the pre-determined pattern of aspiration vacuums based on the linear correlation;
f) comparing a rate of change in the monitored aspiration vacuum to the rate of change of aspiration vacuum stored in the surgical system memory;
g) detecting an occurrence of a surgical event based upon the established match between the monitored aspiration vacuum and the pre-determined pattern of aspiration vacuums and the comparison of the rate of change in the monitored aspiration vacuum to the rate of change of aspiration vacuum stored in the surgical system memory; and
h) varying the operation of the surgical system based on the detection of the occurrence of the surgical event.

4. The method of claim 3 wherein the linear correlation between the monitored aspiration vacuum and the pre-determined pattern of changes in aspiration vacuums is calculated using the following formula, where: N—correlation length (i.e. number of points in the sequences):

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}.$$

5. A method of controlling a surgical system, the surgical system having a memory, comprising the steps of:
a) storing at least one pre-determined pattern of irrigation pressures in the surgical system memory;
b) operating the surgical system to perform a surgical procedure;
c) monitoring the irrigation pressure in the surgical system during the surgical procedure;
d) calculating a linear correlation between the monitored irrigation pressure and the pre-determined pattern of irrigation pressures;
e) establishing a match between the monitored irrigation pressure and the pre-determined pattern of irrigation pressures based on the linear correlation;
f) detecting an occurrence of a surgical event based upon the establishment of the match between the monitored irrigation pressure and the pre-determined pattern of irrigation pressures based on the linear correlation; and
g) varying the operation of the surgical system based on the detection of the occurrence of the surgical event.

6. The method of claim 5 wherein the linear correlation between the monitored irrigation pressure and the pre-determined pattern of irrigation pressures is calculated using the following formula, where: N—correlation length (i.e. number of points in the
    sequences):

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}.$$

7. A method of controlling a surgical system, the surgical system having a memory, comprising the steps of:
a) storing at least one pre-determined pattern of irrigation pressures in the surgical system memory;
b) operating the surgical system to perform a surgical procedure;
c) monitoring the aspiration pressure in the surgical system during the surgical procedure;
d) calculating a linear correlation between the monitored aspiration pressure and the pre-determined pattern of aspiration pressures;
e) establishing a match between the monitored aspiration pressure and the pre-determined pattern of aspiration pressures based on the linear correlation;
f) comparing the rate of change in the monitored irrigation pressure to the rate of change of irrigation pressure stored in the surgical system memory;

g) detecting an occurrence of a surgical event based upon the established match between the monitored irrigation pressure and the pre-determined pattern of irrigation pressures and the comparison of the rate of change in the monitored irrigation pressure to the rate of change of irrigation pressure stored in the surgical system memory; and h) varying the operation of the surgical system based on the detection of the occurrence of the surgical event.

8. The method of claim 7 wherein the linear correlation between the monitored irrigation pressure and the pre-determined pattern of irrigation pressure is calculated using the following formula, where: N—correlation length (i.e. number of points in the sequences):

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}.$$

9. A method of controlling a surgical system, the surgical system having a memory, comprising the steps of:
   a) storing at least one pre-determined pattern of aspiration vacuum and irrigation pressure in the surgical system memory;
   b) operating the surgical system to perform a surgical procedure;
   c) monitoring the aspiration vacuum and irrigation pressure in the surgical system during the surgical procedure;
   d) calculating a linear correlation between the monitored aspiration vacuum and irrigation pressure and the pre-determined pattern of aspiration vacuum and irrigation pressure;
   e) establishing a match between the monitored aspiration vacuum and irrigation pressure and the pre-determined patterns of aspiration vacuum and irrigation pressure based on the linear correlation;
   f) detecting an occurrence of a surgical event based upon the establishment of the match between the monitored aspiration vacuum and irrigation pressure and the pre-determined pattern of aspiration vacuum and irrigation pressure based on the linear correlation; and
   g) varying the operation of the surgical system based on the detection of the occurrence of the surgical event.

10. The method of claim 9 wherein the linear correlation between the monitored aspiration vacuum and irrigation pressure and the pre-determined pattern of aspiration vacuum and irrigation pressure is calculated using the following formula:

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}$$

where N—correlation length(i.e. number of in the sequences).

11. A method of controlling a surgical system, the surgical system having a memory, comprising the steps of:
   a) storing at least one pre-determined pattern of aspiration vacuum and irrigation pressure in the surgical system memory;
   b) operating the surgical system to perform a surgical procedure;
   c) monitoring the aspiration vacuum and irrigation pressure in the surgical system during the surgical procedure;
   d) calculating a linear correlation between the monitored aspiration vacuum and irrigation pressure and the pre-determined patterns of aspiration vacuum and irrigation pressure;
   e) establishing a match between the monitored aspiration vacuum and irrigation pressure and the pre-determined pattern of aspiration vacuum and irrigation pressure based on the linear correlation;
   f) comparing the rate of change in the monitored aspiration vacuum and irrigation pressure to the rate of change of aspiration vacuum and irrigation pressure stored in the surgical system memory;
   g) detecting an occurrence of a surgical event based upon the established match between the monitored aspiration vacuum and irrigation pressure and the pre-determined pattern of aspiration vacuum and irrigation pressure and the comparison of the rate of change in the monitored aspiration vacuum and irrigation pressure to the rate of change of aspiration vacuum and irrigation pressure stored in the surgical system memory; and
   h) varying the operation of the surgical system based on the detection of the occurrence of the surgical event.

12. A method of claim 11 wherein the linear correlation between the monitored aspiration vacuum and irrigation pressure and the pre-determined pattern of aspiration vacuum and irrigation pressure is calculated using the following formula:

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}$$

where: N—correlation length(i.e. number of points in the sequences).

13. A method of controlling a surgical system, the surgical system having a memory, comprising the steps of:
   a) storing at least one pre-determined pattern of aspiration vacuums and at least one rate of change of aspiration vacuum in the surgical system memory;
   b) operating the surgical system to perform a surgical procedure;
   c) monitoring the aspiration vacuum in the surgical system during the surgical procedure;
   d) calculating a linear correlation between the monitored aspiration vacuum and the pre-determined pattern of aspiration vacuums;

e) establishing a match between the monitored aspiration vacuum and the pre-determined pattern of aspiration vacuums based on the linear correlation;
f) calculating a linear correlation coefficient between the monitored aspiration vacuum and the pre-determined pattern of changes in aspiration vacuum;
g) comparing the calculated linear correlation coefficient to the rate of change of aspiration vacuums stored in the surgical system memory;
h) detecting an occurrence of a surgical event based upon the established match between the monitored aspiration vacuum and the pre-determined pattern of of the aspiration vacuums and the comparison of the calculated linear correlation coefficient to the rate of change of aspiration vacuum stored in the surgical system memory; and
i) varying the operation of the surgical system based on the detection of the occurrence of the surgical event.

14. The method of claim 13 wherein the linear correlation coefficient between the monitored aspiration pressure and the pre-determined pattern of aspiration vacuums is calculated using the following formula:

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}$$

where: N—correlation length(i.e. number of points in the sequences).

15. A method of controlling a surgical system, the surgical system having a memory, comprising the steps of:
a) storing at least one pre-determined pattern of irrigation pressures and at least one a rate of change of irrigation pressure in the surgical system memory;
b) operating the surgical system to perform a surgical procedure;
c) monitoring the irrigation pressure in the surgical system during the surgical procedure;
d) calculating a linear correlation between the monitored irrigation pressure and the pre-determined pattern of irrigation pressures;
e) establishing a match between the monitored irrigation pressure and the pre-determined pattern of irrigation pressures based on the linear correlation;
f) calculating a linear correlation coefficient between the monitored irrigation pressure and the pre-determined pattern of changes in irrigation pressure;
g) comparing the calculated linear correlation coefficient to the rate of change of irrigation pressures stored in the surgical system memory;
h) detecting an occurrence of a surgical event based upon the established match between the monitored irrigation pressure and the pre-determined pattern of irrigation pressures and the comparison of the calculated linear correlation coefficient to the rate of change of irrigation pressure stored in the surgical system memory; and
i) varying the operation of the surgical system based on the detection of the occurrence of the surgical event.

16. The method of claim 15 wherein the linear correlation coefficient between the monitored irrigation pressure and the pre-determined pattern of irrigation pressures is calculated using the following formula, where: N—correlation length (i.e. number of points in the sequences):

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}.$$

17. A method of controlling a surgical system, the surgical system having a memory, comprising the steps of:
a) storing at least one pre-determined pattern of aspiration vacuum and irrigation pressure and at least one rate of change of aspiration vacuum and irrigation pressure in the surgical system memory;
b) operating the surgical system to perform a surgical procedure;
c) monitoring the aspiration vacuum and irrigation pressure in the surgical system during the surgical procedure;
d) calculating a linear correlation between the monitored aspiration vacuum and irrigation pressure and the pre-determined pattern of aspiration vacuum and irrigation pressure;
e) establishing a match between the monitored aspiration vacuum and irrigation pressure and the pre-determined pattern of aspiration vacuum and irrigation pressure based on the linear correlation;
f) calculating a linear correlation coefficient between the monitored aspiration vacuum and irrigation pressures and the pre-determined pattern of changes in aspiration vacuum and irrigation pressure;
g) comparing the calculated linear correlation coefficient to the rate of change of aspiration vacuum and irrigation pressure stored in the surgical system memory;
h) detecting an occurrence of a surgical event based upon the established match between the monitored aspiration vacuum and irrigation pressure and the pre-determined pattern of aspiration vacuum and irrigation pressure and the comparison of the calculated linear correlation coefficient to the rate of change of aspiration vacuum and irrigation pressure stored in the surgical system memory; and
i) varying the operation of the surgical system based on the detection of the occurrence of the surgical event.

18. The method of claim 17 wherein the linear correlation coefficient between the monitored aspiration vacuum and irrigation pressure and the pre-determined pattern of aspiration vacuum and irrigation pressure is calculated using the following formula:

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}$$

where: N—correlation length(i.e. number of points in the sequences).

19. A method of controlling a surgical system, comprising the steps of:
   a) operating a surgical system to perform a surgical procedure;
   b) monitoring an aspiration pressure of the surgical system during the surgical procedure;
   c) comparing the monitored aspiration pressure with a pre-determined pattern of changes in aspiration pressure;
   d) varying the operation of the surgical system based on the comparison between the monitored aspiration pressure and the pre-determined pattern of changes in aspiration pressure.

20. A method of controlling a surgical system, the surgical system having a memory, comprising the steps of:
   a) storing at least one pre-determined pattern of aspiration vacuum and irrigation pressure and at least one rate of change of aspiration vacuum and irrigation pressure in the surgical system memory;
   b) operating the surgical system to perform a surgical procedure;
   c) monitoring the aspiration vacuum and irrigation pressure in the surgical system during the surgical procedure;
   d) establishing a match between the monitored aspiration vacuum and irrigation pressure and the pre-determined pattern of aspiration vacuum and irrigation pressure;
   e) detecting an occurrence of a surgical event based upon the established match between the monitored aspiration vacuum and irrigation pressure and the pre-determined pattern of aspiration vacuum and irrigation pressure; and
   f) varying the operation of the surgical system based on the detection of the occurrence of the surgical event.

* * * * *